United States Patent [19]

Wallach

[11] Patent Number: 5,019,174
[45] Date of Patent: May 28, 1991

[54] REMOVING OIL FROM SURFACES WITH LIPOSOMAL CLEANER

[75] Inventor: Donald F. H. Wallach, Brookline, Mass.

[73] Assignee: Micro Vesicular Systems, Inc., Nashua, N.H.

[21] Appl. No.: 410,650

[22] Filed: Sep. 21, 1989

Related U.S. Application Data

[63] Continuation-in-part of Ser. No. 157,571, Mar. 3, 1988, Pat. No. 4,911,928, which is a continuation-in-part of Ser. No. 78,658, Jul. 28, 1987, Pat. No. 4,855,090, which is a continuation-in-part of Ser. No. 25,525, Mar. 13, 1987, abandoned, which is a continuation-in-part of Ser. No. 124,824, Nov. 25, 1987, Pat. No. 4,917,951.

[51] Int. Cl.$^5$ .................. A61K 7/50; A61K 9/127; B08B 7/04
[52] U.S. Cl. ..................... 134/40; 134/42; 252/174.13; 252/312; 252/DIG. 5; 264/4.3; 424/450; 428/402.2; 514/846
[58] Field of Search ............ 264/4.3; 428/402.2; 252/174.13, DIG. 5; 134/40; 424/450; 514/846

[56] References Cited

U.S. PATENT DOCUMENTS

| | | | |
|---|---|---|---|
| 2,980,941 | 4/1961 | Miller | 428/402.2 X |
| 3,528,925 | 9/1970 | Chapuis | 428/402.2 X |
| 3,957,971 | 5/1976 | Cleniacz | 424/70 |
| 4,133,874 | 1/1979 | Miller et al. | 428/402.2 X |
| 4,212,758 | 7/1980 | Shashkina et al. | 252/DIG. 5 |
| 4,217,344 | 8/1980 | Vanlerberghe et al. | 424/60 |
| 4,241,046 | 12/1980 | Papahadjopoulos et al. | 424/450 |
| 4,247,411 | 1/1981 | Vanlerberghe et al. | 252/316 |
| 4,297,374 | 10/1981 | Wess | 514/846 X |
| 4,348,329 | 9/1982 | Chapman | 260/463 |
| 4,356,167 | 10/1982 | Kelly | 424/450 |
| 4,377,567 | 3/1983 | Geho | 424/1.1 |
| 4,485,054 | 11/1984 | Mezei et al. | 264/4.6 |
| 4,536,324 | 8/1985 | Fujiwara et al. | 252/311 |
| 4,551,288 | 11/1985 | Kelly | 264/4.6 |
| 4,564,599 | 1/1986 | Janoff et al. | 436/507 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,666,711 | 5/1987 | Vanlerberghe et al. | 424/70 |
| 4,692,433 | 9/1987 | Hostetler et al. | 514/12 |
| 4,695,554 | 9/1987 | O'Connell et al. | 436/528 |
| 4,772,471 | 9/1988 | Vanlerberghe et al. | 424/450 |
| 4,814,270 | 3/1989 | Piran | 264/4.3 X |
| 4,911,928 | 3/1990 | Wallach | 424/450 |
| 4,942,038 | 7/1990 | Wallach | 252/174.13 X |

FOREIGN PATENT DOCUMENTS

| | | |
|---|---|---|
| 0032578 | 7/1984 | European Pat. Off. |
| 3410602 | 9/1984 | Fed. Rep. of Germany |
| 59-106423 | 6/1984 | Japan |
| 61-207324 | 9/1986 | Japan |
| 85/01440 | 1/1985 | PCT Int'l Appl. |
| 1539625 | 1/1979 | United Kingdom |
| 2078543A | 1/1982 | United Kingdom |
| 2079179A | 1/1982 | United Kingdom |
| 2147263A | 5/1985 | United Kingdom |
| 2166107A | 4/1986 | United Kingdom |

OTHER PUBLICATIONS

Bangham et al. (1965) J. Mol. Biol. 13:238-252.
Gregoriadis (1979) The New England Journal of Medicine 295:704-710.
Szoka, Jr. et al. (1978) Proc. Natl. Acad. Sci. U.S.A. 75:4194-4198.
*Liposomes* (Ostro, ed.) 1983, Marcel Dekker, Inc. New York, pp. 246-249.
Philippot et al. (1983) Biochem. Biophys. Acta 734:137-143.
Ribier et al. (1984) Colloids and Surfaces 10:155-161.
Baillie et al. (1985) J. Pharm. Pharmacol. 37:863-868.
"Methodes de preparation des liposomes", Dousset et al. (Puisieux and Dellattre, Eds.) 1985, Techniques et Documentation La Voisier Paris, pp. 41-72.
"Les niosomes", Handiani-Vila et al. (Puisieux and Dellattre, Eds.) 1985, Techniques et Documentation La Voisier Paris, pp. 297-313.
Philippot et al. (1985) Biochem. Biophys. Acta 821:79-84.
"Problemes technologiques poses par l'utilisation des liposomes comme vecteurs de substances medicamenteuses, Encapsulation, sterilsation, conservation.", Puisieux et al. (Les Liposomes, Eds.) 1985, Techniques et Documentation La Voisier Paris, pp. 73-113.
Baillie et al. (1986) J. Pharm. Pharmacol. 38:502-505.

*Primary Examiner*—Richard D. Lovering
*Attorney, Agent, or Firm*—Lahive & Cockfield

[57] ABSTRACT

The present invention concerns a lipid vesicle skin cleaner which is exceptionally effective at removing oily dirt from hands or the face. The same type of cleaner can also be used to remove dirt from other surfaces. The cleaner works by encapsulating the oil under gentle agitation conditions.

6 Claims, No Drawings

REMOVING OIL FROM SURFACES WITH LIPOSOMAL CLEANER

REFERENCE TO RELATED APPLICATIONS

The present application is a continuation-in-part of U.S. patent application Ser. No. 157,571, filed Mar. 3, 1988, entitled "Paucilamellar Lipid Vesicles," now U.S. Pat. No. 4,911,928, which was a continuation-in-part of U. S. patent application Ser. No. 078,658, filed July 28, 1987, now U.S. Pat. No. 4,855,090, issued Aug. 8, 1989, entitled "Method of Producing High Aqueous Volume Multilamellar Vesicles," which itself was a continuation-in-part of U.S. patent application Ser. No. 025,525, filed Mar. 13, 1987, now abandoned, and U.S. patent application Ser. No. 124,824, filed Nov. 25, 1987, entitled "Lipid Vesicles Formed of Surfactants and Steroids," now U.S. Pat. No. 4,917,951. This application is also related to U.S. patent application Ser. No. 163,806, filed Mar. 3, 1988, entitled "Method and Apparatus for Producing Lipid Vesicles," now U.S. Pat. No. 4,895,452.

BACKGROUND OF THE INVENTION

The present invention relates to a method of removing dirt and oil from surfaces. More particularly, the present invention relates to the use of lipid vesicles or liposomes in a cleaner which can encapsulate the dirt or oil on the surface, thereby removing it.

There are presently two type of detergents used for dirt and oil removal from solid surfaces; the first contain primarily natural or synthetic soaps while the second are the synthetic soapless detergents. Soaps normally consist of sodium or potassium salts of long-chain fatty acids and are now manufactured by saponification of triglycerides from fats with sodium or potassium hydroxide. However, soaps do not function well in acid solutions because of the formation of insoluble fatty acids. In addition, calcium or magnesium ions tend to form a soap scum in the form of an insoluble precipitate. Although additives such as phosphates and sodium carbonate may ameliorate many of these problems, synthetic soapless detergents have been used where soaps are not effective. These synthetic soapless detergents normally have alkyl sulfates, alkyl or aryl sulphonates, or non-ionic polyoxyethylene oxide derivatives as their primary active ingredients.

A good detergent must possess at least three characteristics:

(1) good wetting properties in allow the detergent to contact the surface,
(2) the ability to remove dirt from the surface into the bulk of the liquid, and
(3) the ability to solubilize or disperse the removed dirt to prevent redeposit on the surface, or formation of a scum.

The best wetting agents are those with the shorter fatty acid chains, e.g., $C_8$ versus $C_{14}$ or $C_{16}$. However, the longer chain surface active agents appear to provide better stability for the dirt or oil in the bulk solution once it is removed from the surface. Therefore, one of the problems in detergent science is forming the proper balance between the wetting and stabilization properties.

In practice, the detergent or surface active agent changes the contact angle of the dirt or oil on the surface at the triple solid-oil-water interface, reducing the contact angle so that the oil rolls up into a sphere and can be removed. The materials that act as the best detergents are normally those which form micelles and at one time, there was a theory that the micelles were involved in the cleaning action. In recent years, however, it has become clear that it is the free surfactants which do the cleaning, not those in the micelles. It appears that the micelles merely act as reservoirs of the surface active agents. However, although it is not the surfactants in the micelles which provide the cleaning action, the surfactants do not function as satisfactory oil-in-water emulsifiers, e.g., do not act properly in the stabilization step, until the concentration of the surfactant in the aqueous phase exceeds the critical micelle concentration. Accordingly, micelle formation is normally expected in detergents.

In standard detergent action, oil-in-water emulsions are formed to stabilize the oily dirt particles and maintain them in solutions. The surfactants act to lower the surface tension of the water and the interfacial tension between the water and oil. However, there is no true vesicle formation or even micellar entrapment of the dirt using most detergents.

Until the methods and products described in the Previously cited U.S. patent application Ser. No. 157,571, now U.S. Pat. No. 4,911,928, there had been no description of lipid vesicles or liposomes which could encapsulate oil, except for the small amount of lipid which could be incorporated into the lipid bilayers before bilayer breakdown. However, U.S. patent application Ser. No. 157,571, now U.S. Pat. No. 4,911,928, describes paucilamellar lipid vesicles having large amorphous oil-filled centers which could carry substantial quantities of oily material. These vesicles, which have 2–10 lipid bilayers surrounding a large, amorphous central cavity, are stable and can be formed under conditions which are so rapid that they are cost-effective for use in industrial applications.

Accordingly, an object of the invention is to provide a surface cleaning solution which contains lipid vesicles or liposomes.

Another object of the invention is to provide a surface cleaning agent which encapsulates oil or dirt in lipid vesicles to remove it from the surface.

A further object of the invention is a method of cleaning hand using a lipid vesicle skin cleaner to encapsulate grease or dirt.

These and other objects and features of the invention will be apparent from the following description.

SUMMARY OF THE INVENTION

The present invention features a method of removing oil from a surface through liposomal encapsulation of the oil or dirt. Preferably, lipid vesicles or liposomes are introduced to the surface to be cleaning where they are broken or fractured and reformed, thereby encapsulating the oil present and removing the dirt. In certain circumstances, the vesicles are formed and encapsulate the oil in situ. This method is particularly good for cleaning hands of oil and other types of greasy dirt.

The present method of removing oil from the surface has the steps of providing paucilamellar lipid vesicles having 2–10 bilayers surrounding a large, amorphous center at the surface to be cleaned. Normally, prepared vesicles are introduced to the surface but using certain materials and under selected conditions, the vesicle-making material itself can be introduced to the surface and the vesicles form in situ, encapsulating the dirt or oil as they are formed. While these vesicles normally have an aqueous solution filling the center, an aqueous or oil-based detergent or cleaner could be encapsulated within the large amorphous central cavity. Although almost any non-phospholipid surfactant could be used as the major component of the vesicle walls, the preferred surfactants are polyoxyethylene fatty acid ethers, polyoxyethylene fatty acid esters, diethanolamides, polyoxyethylene glyceryl monostearates, and betaines, particularly oleoyl propyl betaine. The vesicle bilayers may also include charge-producing agents such as fatty acids or dicetyl phosphate and a steroid such as cholesterol or its derivatives.

Once the vesicles introduced to the surface, they are normally agitated, preferably in the presence of an aqueous solution, with sufficient force so at least a portion of the paucilamellar vesicles fracture and reform. These reformed vesicles encapsulate the oily dirt from the surface, thereby cleansing the surface. If the vesicles are formed in situ, the vesicle forming solution is introduced to the surface and the agitation must be sufficient to provide shear mixing and the accompanying vesicle formation. The vesicles are then removed, e.g., by washing with an aqueous solution, thereby removing the dirt along with the vesicles. The preferred surface is mammalian skin, e.g., the hands or face, and the agitation is then provided by rubbing. The removal step is, in that case, applying an aqueous solvent such as water to the hands after the agitation step. The removal step may also take place by applying an aqueous solvent contained in a carrier material such as a sponge or a wipe.

The method of the invention provides cleaning without the use of a separate soap or an organic cleaner such as D-limonene; however, in certain circumstances, a soap or other detergent may be used to assist in the step of removing the vesicles from the surface.

The following description will more clearly illustrate the invention.

DETAILED DESCRIPTION OF THE INVENTION

The method of the present invention is particularly well suited to hand cleaning but may used for cleaning other surfaces where oil or grease build-up is a problem. Hand cleaning is preferred because the agitation step of the invention is most easily carried out by rubbing the hands together as one normally does during daily ablutions.

As noted, almost any non-phospholipid surfactant may be used as the major lipid component of the bilayers of the paucilamellar lipid vesicles used in the invention, but vesicles made of polyoxyethylene fatty acid ethers, polyoxyethylene fatty acid esters, diethanolamides, polyoxyethylene glyceryl monostearates, and betaines are most preferred. Although any method could be used to manufacture paucilamellar lipid vesicles having these surfactants as their major structural component of the bilayers, the methods and materials described in U.S. patent application Ser. No. 157,571, now U.S. Pat. No. 4,911,928, incorporated herein by reference, are preferred. Briefly, the surfactant and any other lipophilic materials to be incorporated into the vessel walls are blended, preferably at elevated temperature to improve flowability If a water-immiscible oily material, e.g., an oily cleaner, is to be added to the center of the vesicles initially (i.e., before application of the vesicles to the surface), it is dispersed with the lipophilic phase of the surfactants at this time. The lipophilic phase is then blended, under shear mixing conditions, with an excess of an aqueous phase. The aqueous phase includes any aqueous soluble materials which are to be included within the vesicle, e.g., any aqueous hand cleaner or second surfactant. The shear mixing provides sufficient hydration of the surfactant to form the vesicles and the vesicles form extremely rapidly, in certain circumstances in milliseconds. Although small batches can be made by placing the lipophilic phase in one syringe, the aqueous phase in another, larger syringe, and forceably injecting the material back and forth through a stopcock for approximately a minute, the apparatus and methods described in U.S. patent application Ser. No. 163,806, now U.S. Pat. No. 4,895,452, also incorporated herein by reference, are preferred. The mixing device has a substantially cylindrical central chamber with tangentially located inlet jets about its outer surface. The lipophilic phase and the aqueous phase are injected into the chamber with sufficient velocity so that turbulence is formed in the chamber, hydrating the surfactant and forming the vesicles. The vesicles are withdrawn through an axially located outlet tube. The formed vesicles then can be apPlied to the surface to be cleaned.

The following Examples will more clearly illustrate the invention.

EXAMPLE 1

In this Example, used crank case oil was spread on the palms of hands until filthy but not dripping. This required about 1 ml of the crank case oil per hand. Approximately 1 ml of a solution of lipid vesicles made from polyoxyethylene-2 cetyl ether (Brij 52-ICI Americas), cholesterol, and oleic acid in a ratio of 30:11:1, approximately 45% moisture, was placed on each palm. The vesicles were made using the previously described procedures and had an aqueous filled central cavity. The palms were rubbed together to distribute the vesicles over the dirty area and rubbing was continued for approximately one minute After rubbing, the palms were rinsed with warm water and wiped clean. Under certain circumstances, dry toweling alone is sufficient.

This procedure removed substantially all of the crank case oil from the hands without the need for rinsing with soap. Old axle grease can be cleaned the same way.

EXAMPLE 2

In this Example, a semi-quantitative method was used to determine the encapsulation of oil by the vesicles.

Approximately 2 ml of used crank case oil was blended with 5 ml of the polyoxyethylene-2 cetyl ether aqueous filled vesicles, made as described above, by springing back and forth for two minutes. The yield is a brown, thick solution. After centrifugation at 3,000 rpm for thirty minutes, no free oil was observed by microscopy. When 3 ml of crank case oil was used in place of the 2 ml of oil, approximately 0.2 ml of free oil was observed after centrifugation.

The replacement of the polyoxyethylene-2 cetyl ether with a polyoxyethylene-9 glyceryl monostearate and monooleate yields the same results except a full 4 ml of oil can be taken up by the 5 ml of lipid vesicles without any free oil being observed after centrifugation.

In either case, oil filled paucilamellar vesicles rather than non-vesicular structures are observed under a microscope.

EXAMPLE 3

In this Example, a series of paucilamellar lipid vesicles filled with different materials were used in order to determine the effectiveness of the claimed procedure. All of the vesicles were made with polyoxyethylene-9 glyceryl monostearate and monooleate, cholesterol, and oleic acid in a ratio of 30:11:1 using the procedures described previously. The first sample had vesicles 15% by weight of petrolatum, a vaseline-like petroleum jelly, encapsulated in the central cavity. The second sample had 60% by weight encapsulated petrolatum, while the third sample had 20% by weight encapsulated D-limonene, a turpentine oil derivative which is used as a hand cleaner The fourth vesicle sample had an aqueous center with no other material encapsulated while the fifth had a combination of 20% D-limonene and 2% mineral oil (Drakeol 19) encapsulated.

In each of the tests, 1 ml of crank case oil was spread evenly on each hand The 5 ml of the vesicles (approximately 45% moisture) was added to the hands and the hands were scrubbed for together approximately 45 seconds. The mixture which formed was collected into a test tube using a spatula and centrifuged at 3,500 rpm for twenty minutes before microscopic examination. The hands were then cleaned with warm water and soap as required.

For the 15% petrolatum vesicles, no oil separation was observed on centrifugation, showing complete encapsulation of the crank case oil by the vesicles. The hands could be washed clean only with a soap rinse. Post centrifugation microscopic examination showed large, oddly shaped vesicles.

The 60% petrolatum vesicles did not work as well as the 15% petrolatum vesicles. Although there was no oil separation upon centrifugation, the hands became quite sticky and rinsing was not easy, requiring two to three soap washes. Microscopic examination showed huge, oddly shaped vesicles.

The 20% D-limonene vesicles (sample 3) as well as the 20% D-limonene with 2% mineral oil (sample 5) vesicles did not do as well. For the vesicles without the mineral oil, everything became quite fluid upon scrubbing and started dripping off the hands. While cleaning was effective with only one soap rinse, approximately $\frac{1}{4}$ ml of oil separated as a supernatant upon centrifugation. Microscopic examination showed very few vesicles with a large number of non-vesicle structures. Substantially similar results were obtained with the D-limonene/mineral oil vesicles except approximately $\frac{1}{2}$ ml of oil separation occurred as a supernatant.

The best cleaning came from the aqueous filled vesicles. Upon centrifugation, no oil separation was observed and microscopic examination showed small, substantially uniform oil filled vesicles. Cleaning was effective using these vesicles alone and the hands could be cleaned with just a warm water rinse (no soap). As previously discussed in Example 1, dry toweling itself can remove the oil.

EXAMPLE 4

In this experiment, a series of solutions which can be used to make lipid vesicles under the conditions described in U.S. patent application Ser. No. 157,571, now U.S. Pat. No. 4,911,928, were tested as cleaners. This experiment shows that the vesicles may be made and encapsulate dirt or oil in situ under certain circumstances while still providing the hand cleaning action.

Approximately 1 ml of crank case oil was spread evenly over both hands. The hands were then wet with 3 ml of water. One ml of the test sample, heated if necessary to be in the liquid phase, was added to hands and the hands were scrubbed for approximately 45 seconds. Additional water was added if the mixture was too thick. The mixtures were collected into a test tube using a spatula and centrifuged at 3,500 rpm for twenty minutes. The sample was then examined microscopically for oil separation and vesicle structure, and the hands were cleaned as necessary.

The first test solution was the stock solution which had been used to make the vesicles before application in Example 3. This stock solution had polyoxyethylene-9 glyceryl monostearate and monooleate, cholesterol, and oleic acid in a 30:11:1 ratio. It was heated with flowability (above 45° C.) and applied to the hands. Upon centrifugation, no oil separation was seen. The hands could be washed clean with one soap rinse (as compared with the ability to clean without the use of soap by applying the vesicles themselves). Microscopic examination showed spherical vesicles with some having the appearance of standard oil-filled lipid vesicles.

The next two samples were similar to that used in Example 1. First, a polyoxyethylene-2 cetyl ether, cholesterol, and oleic acid solution in 30:11:1 ratio was tested. Again, the sample was heated to about 45° C. for flowability. Again, there was no oil separation on centrifugation and the hands could be washed clean with one soap rinse. Microscopic examination showed oil-filled vesicles. Without the cholesterol and oleic acid, the polyoxyethylene-2 cetyl ether was not as effective. There was a very small amount of oil separation upon centrifugation but it was difficult to clean the hands even with soap. All of the structures were microemulsion structures rather than vesicles.

A polyoxyethylene-4 lauryl ether, cholesterol, and oleic acid mixture in a 30:11:1 ratio, as well as a polyoxyethylene-4 lauryl ether itself, were also tested. With the cholesterol and oleic acid added, there was approximately $\frac{1}{2}$ ml of oil separation upon centrifugation. However, the hands could be washed clean with warm water only and microscopic examination showed good vesicles with some having internal multiemulsion structures. In contrast, by using the lauryl ether alone without the cholesterol and oleic acid, there was no visible oil separation on centrifugation. The hands could be washed clean with warm water only (or just dry toweling) and microscopic examination showed good vesicles with multiemulsion structures.

The results of these experiments show that by judicious selection of the initial materials, oil-filled vesicles could be manufactured in situ and achieve the method of the invention. However, since most of these materials must be heated to approximately 45° C., the use of the stock solutions rather than the preformed vesicles, which can be used at room temperature, is not as preferable.

The foregoing Examples are purely illustrative and are not meant to limit the invention. The invention is defined by the following claims.

What is claimed is:

1. A method of removing oil from a surface comprising the steps of:
   A. Providing paucilamellar lipid vesicles having 2-10 lipid bilayers surrounding a large, substantially aqueous filled amorphous center, said paucilamellar lipid vesicles having a lipid selected from the group consisting of polyoxyethylene fatty acid ethers, polyoxyethylene fatty acid esters, diethanolamides, polyoxyethylene glyceryl mono- and tristearates and oleates, and betaines as the primary structural lipid in the bilayers;

B. Introducing said paucilamellar vesicles to said surface;

C. Agitating said paucilamellar lipid vesicles on said surface with sufficient force such that at least a portion of said paucilamellar vesicles are broken and reform under said agitation, whereby said reformed vesicles encapsulate said oil; and D. Removing said vesicles containing said encapsulated oil from said surface.

2. The method of claim 1 wherein said surface comprises mammalian skin, said agitation step comprises rubbing, and said removal step comprises applying an aqueous solvent.

3. The method of claim 2 wherein said removal step comprises washing said skin with water.

4. The method of claim 2 wherein said removal step comprises applying said aqueous solvent by wiping said skin with a material containing said aqueous solvent.

5. The method of claim 2 wherein said mammalian skin comprises human skin.

6. The method of claim 1, wherein said paucilamellar lipid vesicles further comprise an encapsulated cleanser.

* * * * *